United States Patent [19]
Kolberg et al.

[11] Patent Number: 6,053,895
[45] Date of Patent: Apr. 25, 2000

[54] SYRINGE WITH A NEW AND IMPROVED PLUG

[75] Inventors: Reiner Kolberg; Ralf-Siegbert Hauck, both of Berlin, Germany

[73] Assignee: Schering Aktiengesellschaft, Berlin, Germany

[21] Appl. No.: 08/953,429

[22] Filed: Oct. 17, 1997

Related U.S. Application Data

[60] Provisional application No. 60/030,383, Nov. 5, 1996.

[51] Int. Cl.[7] .................................................. A61M 5/315
[52] U.S. Cl. .......................................... 604/218; 604/230
[58] Field of Search .................................. 604/187, 218, 604/219, 222, 230

[56] References Cited

U.S. PATENT DOCUMENTS

| | | | |
|---|---|---|---|
| 546,603 | 9/1895 | Tagliabue | 604/230 |
| 4,500,310 | 2/1985 | Christinger | 604/228 |
| 5,009,646 | 4/1991 | Sudo et al. | 604/230 |
| 5,147,328 | 9/1992 | Dragosits et al. | 604/230 |
| 5,256,157 | 10/1993 | Samiotes et al. | 604/151 |
| 5,397,313 | 3/1995 | Gross | 604/218 |
| 5,620,423 | 4/1997 | Eykmann et al. | 604/222 |
| 5,713,857 | 2/1998 | Grimard et al. | 604/218 |
| 5,735,825 | 4/1998 | Stevens et al. | 604/218 |

*Primary Examiner*—Wynn Wood Coggins
*Assistant Examiner*—Sharon Finkel
*Attorney, Agent, or Firm*—Millen, White, Zelano & Branigan

[57] ABSTRACT

A medicinal syringe includes a cylinder with a proximal and distal end, and an outlet. The syringe contains, or is adapted to receive, a medicine or a diagnostic agent, and includes a plug. The surfaces of plug which touch the inside wall of the cylinder are preferably made of polytetrafluoroethylene. The material for the cylinder inside wall directly adjoins the surfaces of the plug, which touch the inside wall of the cylinder. The plug has at least one sealing lip and the mass-resultant of the sealing lip forms an acute angle with the axis of the syringe in that distal direction.

15 Claims, 5 Drawing Sheets

SYRINGE WITH A NEW AND IMPROVED PLUG

REFERENCE TO RELATED APPLICATIONS

This application is entitled to the benefit of the date of U.S. Provisional Application Ser. No. 60/030,383 filed Nov. 5, 1996.

The invention relates to a medical syringe for receiving a medium or for use and a process for terminal sterilization of this filled syringe. These syringes are preferably provided for administering injectable diagnostic agents, especially contrast media, which are injected into, for example, blood vessels, organs, organ parts, cavities and other vessels, or which exert an imaging action there.

BACKGROUND OF THE INVENTION

German Patent DE 3346 351 with a publication date of Apr. 9, 1992 describes a plug that is provided at least partially with a teflon coating. Such a plug touches the inside wall of the cylinder with beads that exert a specific pressure on the inside wall of the cylinder, thus ensuring the sealing effect. The beads are designed in such a way that the perpendicular lines of the bead surface that face away from the plug face toward the wall of the barrel. The patent uses teflon to provide a protective surface between the medium and the rubber portion of the plug. This is thus exclusively an insulating function; the excellent sliding properties of teflon are not taken into consideration any further here. In this publication, the term siliconization was not mentioned. It is thus to be assumed that even in this case, one skilled in the art would read this text to mean that this is a syringe that corresponds otherwise to the general technical knowledge (e.g., DIN Standard 13 098, Part 1, Item 4.4) and that is also siliconized on the inside of the cylinder.

DE-GM 19 73 042 dated Nov. 23, 1967 describes a plastic syringe made of synthetic resin, which consists of a plastic cylinder with a needle opening and a plug opening, a plug, and a plunger. The syringe has, as a basic feature, a shell-shaped or bowl-shaped plug that is made of commercially available material. Such a sealing lip is feasible, however, only in combination with a lubricant, especially with silicone oil. If silicone oil is not present, the sealing lips would be distorted because of the great friction and, giving way to the force, they would tip over. In this publication, the term siliconization also was not mentioned. Thus, it is also to be assumed here that one skilled in the art would read this text to mean that this is a syringe that otherwise corresponds to the general technical knowledge (e.g., DIN Standard 13 098, Part 1, Item 4.4) and that is also siliconized on the inside of the cylinder.

Patent AT-E 68 979 describes a filled, terminally sterilized syringe. The syringe is made of plastic. The syringe has a cylinder with a distal end with a syringe outlet piece. The syringe outlet piece is sealed with a closure. Before filling, the inside wall of the syringe is coated with silicone oil. After filling, the syringe is sealed with a flexible rubber plug, which is also able to slide into the cylinder because of the silicone oil.

The process for the production of a filled, terminally sterilized syringe thus begins with waste particles or other contaminants being removed from the closure and the plunger. Microbial contaminants on the closure and the plunger are destroyed. The cylinder is washed with a considerable number of water jets to remove pyrogens and waste particles. Then, silicone oil is applied on the inside wall of the syringe. The closure is then slipped onto the syringe outlet piece. The contrast medium is filled in the syringe through the proximal end of the syringe. The syringe is then sealed with the plug. This assembled and filled syringe is sterilized in an autoclave. In this case, in addition to the commonly used autoclave pressure, an additional supporting pressure is generated in the autoclave.

Prefilled, terminally sterilized cartridge-needle units that are provided with a silicone oil layer on the inside wall are known from the publication by Venten and Hoppert (E. VENTEN and J. HOPPERT (1978) Pharm. Ind. Vol. 40, No. 6, pages 665 to 671). The cartridge-needle units, which have a plug on the proximal end, are filled distally via the rolled edge. The rolled edge is then sealed with a sealing disk, whereby a flange cap attaches the sealing disk to the rolled edge. (M. JUNGA (1973) Pharm. Ind. Vol. 35, No. 11a, pages 824 to 829). The prefilled cartridge-needle units are then moved into an autoclave. This autoclave can be adjusted in terms of temperature and pressure.

European Patent Application EP 0553 926 (date of application: Jan. 26, 1993) describes a process for terminal sterilization of a prefilled plastic syringe or glass syringe, whereby the syringe contains a contrast medium. The inside wall of the disposable syringe is coated with silicone oil. The syringe consists of a barrel that has a syringe outlet piece at the distal end. In addition, disposable cartridge-needle units are indicated in the form already described above by Venten and Hoppert. The disposable syringes have an open proximal end, which can be sealed by a plug that can slide into the disposable syringe. The plug is connected to a plunger.

WO 95/12482 describes a process for the production of prefilled plastic syringes that are filled with a contrast medium. The inside wall of the syringe is coated with silicone oil. The syringes consist of a cylinder, a syringe outlet piece at the distal end, which is prepared for a cannula attachment. The syringe also comprises a plug that can slide into the cylinder. It seals the proximal end of the syringe. The syringe was produced according to a process that results in pyrogen-free objects. Also, no more particles are present. The syringe is filled via the proximal end; in this case, the syringe outlet piece is sealed with a closure. The filled syringe is sealed with the plug.

After the syringe parts come out of the die, gas is blown over them to remove particles. The syringe is then washed and provided with lubricant. The syringe is then sterilized in such a way that the syringe can be further processed, stored, or transported, as desired.

Drawbacks

Disadvantageous in the case of the known syringes is that silicone oil must be used to reduce the friction between the plug and the inside wall of the syringe. Although a rubber plug is reasonable in view of the elastic forces, behavior relative to sliding friction is problematical. Adhesive friction is even more of a problem. Especially in the case of prolonged storage of the syringe with an inserted plug, adhesive friction plays a very important role. In addition, consideration should always be given to cold-flow behavior in the case of rubber plugs. Since the latter factor is not insignificant, rubber plugs with considerable prestressing must be used. In this case, friction in all cases is so great that, without silicone oil, handling of the syringes is not possible.

Even if sealing lips made of rubber are used, the latter in the static state do not seal adequately or suffer from cold-flow behavior. Also in this case, work is to be done with considerable prestressing, so that silicone oil is indispensable in this case as well.

A solid plug that is made of teflon has a considerable disadvantage in the case of syringes that are exposed to thermal stress. Here, even temperature fluctuations of from −10° C. to +40° C. are sufficient to allow the plastics of the syringe wall to expand relative to the very solid teflon material. These are common temperature fluctuations. Also in this case, the cold-flow behavior becomes apparent in a negative way. To allow the plug to seal well, great prestressing, which means great friction, is necessary because of the slightly elastic behavior of the solid teflon plug. Such a teflon plug is not to be used in plastic syringes since the cold-flow behavior of the syringe wall that is made of plastic increases the inside diameter of the syringe at the level of the plug. As a result, gaps form through which liquid can pass uncontrolled from the syringe. As a result, uncontrolled air can also be aspirated. Glass syringes, which do not exhibit such cold-flow behavior, must still be coated with silicone oil on the inside wall to reduce friction, which is caused by the very high prestressing.

SUMMARY OF THE INVENTION

An object is thus to offer a medical syringe, in which the addition of a lubricant in the form of, for example, silicone oil, is unnecessary, without thereby impairing the ability of the plug, which is to be made of plastic, to slide in the syringe and at the same time ensuring adequate sealing of the contents of the syringe by the plug relative to the outside area of the syringe.

This object and other objects are achieved by a medical syringe with an inserted plug, whereby the syringe comprises the following features:
 a) the syringe comprises
  (i) a cylinder with an inside wall of the cylinder,
  (ii) a proximal end,
  (iii) a distal end, and
  (iv) an outlet,
 b) the syringe is prepared for receiving a medium,
 c) at least the surfaces of the plug that touch the inside wall of the barrel are made of polytetrafluoroethylene or of substituted polyethylene or polypropylene, whereby the hydrogen atoms of the polyethylene or polypropylene are substituted at least partially by fluorine atoms,
 d) the material of the inside wall of the cylinder directly adjoins the surfaces of the plug that touch the inside wall of the barrel,
 e) the plug has at least one sealing lip, which seals against the inside wall of the barrel,
 f) at least the surfaces that face distally or proximally or the mass-resultant of the sealing lip forms an angle with the axis of the syringe,
  which is smaller than a right angle, or
 f') the elastic forces that press the sealing lip against the inside wall of the cylinder are caused by an area of the sealing lip,
  said area lies outside the perpendicular lines to the inside wall of the cylinder,
   whereby the perpendicular lines run through the contact area between sealing lip and inside wall of the cylinder, or
 f") the elastic forces which, with the plug in the static state, press the sealing lip against the inside wall of the cylinder are caused by an elasticity area that has a pulling zone in addition to a compressing zone.

Items f); f'); and f") are alternative descriptions of one and the same technical solution principle. More preferred is the description of f'); most preferred is the description from item f").

A More Special Embodiment

Preferred is a more special embodiment of a medical syringe that is made of glass and/or plastic with an inserted plug, with the following features:
 a) the syringe comprises
  (i) a cylinder with the inside wall of a cylinder,
  (ii) a proximal end, which can be sealed by the plug,
  (iii) a distal end, which is sealed by a cylinder cover, and
  (iv) an outlet, which penetrates the cylinder cover or the inside wall of the cylinder,
 b) the syringe is prepared for receiving a medium or for use,
 c) at least the surfaces of the plug that touch the inside wall of the barrel are made of polytetrafluoroethylene or of substituted polyethylene or polypropylene, whereby the hydrogen atoms of the polyethylene or polypropylene are substituted at least partially by fluorine atoms,
 d) the material of the inside wall of the cylinder in the area of the cylinder sheath directly adjoins the surfaces of the plug that touch the inside wall of the barrel,
 e) the plug has at least one annular sealing lip, which seals against the inside wall of the barrel,
  so that when the plug moves in the distal direction, no medium can slip past the sealing lip unless the inside wall has an outward bulge,
 f) at least the surfaces that face distally or proximally or the mass-resultant of the sealing lip forms an angle with the axis of the syringe,
  which is smaller than a right angle, or
 f') the elastic forces that press the sealing lip against the inside wall of the cylinder are caused by an area of the sealing lip,
  said area lies outside the perpendicular lines to the inside wall of the cylinder,
   whereby the perpendicular lines run through the contact area between sealing lip and inside wall of the cylinder, or
 f") the elastic forces which, with the plug in the static state, press the sealing lip against the inside wall of the cylinder are caused by an elasticity area which has a pulling zone in addition to a compressing zone.

The object is also achieved by a medical syringe with an inserted plug, which minimize lubricant whereby the syringe comprises the following features:
 a) the syringe comprises
  (i) a cylinder with the inside wall of a cylinder,
  (ii) a proximal end,
  (iii) a distal end, and
  (iv) an outlet,
 b) the syringe is prepared for receiving a medium,
 c) at least the surfaces of the plug that touch the inside wall of the barrel are made of polytetrafluoroethylene or of substituted polyethylene or polypropylene, whereby the hydrogen atoms of the polyethylene or polypropylene are substituted at least partially by fluorine atoms,
 d) between the surfaces of the plug that touch the inside wall of the barrel and the inside wall of the cylinder, there is no lubricant or
  a lubricant of at maximum such a thickness that, in the event that the plug moves in the syringe in the way that is usual in practice, it no longer allows satisfactory sliding friction and adhesive friction, which would arise when a rubber plug was used, or a lubricant of such a thickness, that does not allow the plug to move in the syringe under conditions that are common in use if the plug were made of rubber, e) the plug has at least one sealing lip, which seals against the inside wall of the barrel, f) at least the surfaces that face distally or proximally or the mass-resultant of the sealing lip forms an angle with the axis of the syringe,
   which is smaller than a right angle, or f') the elastic forces that press the sealing lip against the inside wall of the cylinder are caused by an area of the sealing lip,
   said area lies outside the perpendicular lines to the inside wall of the cylinder,
   whereby the perpendicular lines run through the contact area between sealing lip and inside wall of the cylinder, or f") the elastic forces which, with the plug in the static state, press the sealing lip against the inside wall of the cylinder are caused by an elasticity area which has a pulling zone in addition to a compressing zone.

Advantages

Elimination of lubricant:

The fact that the plug rests directly on the inside wall of the syringe means that lubricant is unnecessary. In this case, lubricants can be fats, silicone oil, or fine granulates. A disadvantageous aspect of all these lubricants is that they can interact with the medium in the syringe. This is especially important if the medium is in direct contact with the lubricant over a prolonged period. In this case, because of the prior art, it is usual to apply the lubricant to the inside wall of the syringe, thereby producing a large surface that is in contact with the medium.

Improvement of the solid plug without a sealing lip:

The plugs in DE 33 46 351 are not to be used if the syringe is autoclaved in prefilled form or is exposed to terminal stressing. In such a situation, bulging of the material always occurs since the plastics of the barrel or the plug have flow properties at elevated temperatures. For this purpose, the plastic is permanent at least at the plug and occasionally also at the syringe and remains deformed. Also, the teflon in the form of coating is among the substances that are changed during autoclaving because of the thermal action.

Because the plug must be over-sized, expansions that result in permanent damage to the plug because of the flow behavior of the plug are produced during the autoclaving cycle or the thermal stress. In many cases, this results in leaks since material exits from the prefilled syringe or air from the outside area optionally penetrates the syringe. In both cases, these are contaminations that are undesirable. Especially in the latter case, air may penetrate. As a result, contamination of the syringe contents can occur, which is highly dangerous to patients. Based on tests that we conducted in-house, it has turned out that solid plugs that are made either of teflon or are teflon-coated cannot be used for syringes that are autoclaved in the prefilled state or are exposed to thermal stresses. Tests have also been carried out that also revealed problems in the case of syringes that are not prefilled as disposable syringes.

Material polytetrafluoroethylene and fluorine-substituted polyethylenes or polypropylenes:

The selection of the material for the plug is limited. Polytetrafluoroethylene and its modifications are especially suitable since their temperature stability is very high. Autoclaving of the plug according to the invention is readily possible. The plugs are stable; while they do exhibit cold-flow behavior, given the requirements that are imposed such behavior is virtually negligible. Thus, the plugs are also stable in storage for a long time in direct contact with the syringe body. The sealing function of the plug is not impaired. The plugs are compatible to humans; polytetrafluoroethylene is approved by the U.S. health authorities (FDA). The resetting capability of polytetrafluoroethylene is respectable; as a result, its shelf life is also positively influenced. Polytetrafluoroethylene exhibits good sliding properties, meaning that the forces that arise on the inside wall of the syringe can be relatively large without, in this case, the movement of the plug in the distal or proximal direction having too negative an influence. The cold-flow behavior of the material is gratifyingly slight, so that even this aspect has a beneficial effect on shelf life.

The forces that are exerted by the plug according to the invention on the inside wall of the cylinder are considerably smaller than those that arise in the case of other conventional elastomers. This is possible because of the material used and the configuration of the sealing lips.

By itself, however, shaping of the sealing lips according to the prior art is not sufficient to achieve such an effect. Only when lubricants are added to the inside wall of the syringe or to the outside of the plug can such good proportions develop between the forces in the longitudinal direction of the cylinder and the forces in the direction of the inside wall of the cylinder.

A syringe according to the invention in which the sealing lip faces toward the distal end and which has a surface that faces the axis of the syringe and which passes on the force that develops owing to the internal pressure of the syringe (during use or during autoclaving) toward the inside wall is advantageous.

Unsatisfactory sealing lips made of rubber:

A syringe according to DE-GM 19 73 042 dated Nov. 23, 1967 cannot be autoclaved in prefilled form. It is possible that during the heating and sterilization phase the bowl-shaped plug will move in the proximal direction under the action of the internal pressure. In this case, at this moment, the sealing function is ensured. In the course of cooling, the liquid and particularly also the residual gas draw together in the syringe, thereby creating a partial vacuum relative to the surrounding atmosphere. The effect of this is that suction is exerted on the plug. Also, in the case of a siliconized inside wall, the result is that such a syringe draws in air along the sides of the sealing lips. Such an effect is basically unavoidable if silicone oil is not used.

If no lubricant is used, the bulges of the bowl-shaped plug bend when they move distally since the friction between plug and inside wall of the cylinder is so great that the bulges slip owing to the elasticity.

Even small amounts of lubricant have the following effect according to the invention:

A simple work-around in the invention, if in the text of the claims it is limited only to the omission of a lubricant, consisted of reducing the amount of lubricant to such an extent that it would no longer be adequate for a rubber plug. Since no lubricant is necessary for the teflon plug or plugs made from derivatives of TEFLON®, a small amount of lubricant would be a way to offer a deteriorating embodiment. Since the toxicity of all substances depends on concentration, an amount of lubricant can thus easily be selected which is not physiologically significant and which at the same time is not adequate for a rubber plug but which would, of course, be usable in connection with a teflon plug.

Synergism of TEFLON® and sealing lips:

The combination of the material and the specifically deformed sealing lips ensures that otherwise problematical syringes that are autoclaved in, for example, the prefilled state can be produced and stored without failure.

We have the interaction of three different parameters.

On the one hand, there is the material. Here, TEFLON® or its derivatives are especially advantageous because of the inert behavior of teflon relative to medicines. In addition, TEFLON® has a low coefficient of friction. If the technical teaching of the prior art is followed, however, and plugs are produced from teflon in the conventional form, a satisfactory result cannot be achieved. Leaks and undesirable aspiration of liquid or air can be observed as a drawback.

The second aspect is therefore also important. The shape of the sealing lip must be such that, owing to the cold-flow behavior and the elasticity that results from it, the sealing lips are pressed adequately against the inside wall of the syringe. In this case, especially in the case of prefilled, sterilized syringes, the static tightness is of special importance. Prolonged storage and thermal treatment need not result in leaks. Because of the special embodiments of the sealing lips when the material is specially selected, it is ensured that the tightness of the plug is adequate. This is not just sealing in a direction that arises when, e.g., the syringe contents are injected, but also tightness during aspiration. This is also especially important when the plug moves during autoclaving or during the aspiration of liquid. During autoclaving, the plug follows a force parallelogram that consists of the internal pressure of the syringe and the outside pressure in the autoclave. To keep excessive pressures from arising in the syringe, the plug moves outward during the heating and sterilization phase. During the cooling phase, however, the reverse direction of movement can be observed. A comparable kind of behavior occurs when liquids are aspirated.

The fact that it is not coated with silicone oil can be seen as a third important aspect. The use of lubricant is generally common in the case of previously known syringes with plastic plugs. This is evident from the DIN standards (for example, DIN Standard 13 098). Only the old glass syringes with metal plugs were not siliconized.

Definitions

Direction of the sealing lips:

The sealing lips usually have a basically triangular cross-section. The base faces toward the center of the plug, and the two legs meet at the tip of the sealing lips. The surfaces of the sealing lips can be turned in a straight line or else bent. It is preferable for the sealing lips to be considerably broader at their base than at their tips. This has the effect that the sealing is especially effective, without incurring a high material cost. This base is referred to as a sealing lip attachment point.

Instead of having the sealing lips taper off at their end, it is also possible to arrange a reinforcement piece that has the effect that the tip of the sealing lip is also pressed against the inside wall of the cylinder. This reinforcement piece thus has the function of providing another elasticity area. It is also possible to produce the reinforcement piece from another elastic material, i.e., from a highly elastic rubber, which can be supported at the center of the plug and which at the inside of the sealing lip presses the sealing lip against the inside wall of the cylinder.

A sealing lip that is made relatively long and that has a relatively flat angle relative to the axis of the plug is desirable. This ensures that two functions are met. On the one hand, in dynamic behavior, the sealing lip is pressed against the inside wall of the cylinder owing to the pressure in the syringe. In addition, in the static system, a reasonable compromise has been struck between elasticity and plasticity. This is especially important if additional stresses, such as autoclaving, thermal stress (temperature during normal storage), pressure and solar radiation, stress the material in terms of plasticity.

Another characterization of the direction of the sealing lips can be provided with the aid of the mass-resultants. If the sealing lip is considered in its cross-section, a line that lies in the center of the two sides can be drawn from the base of the sealing lip, which is inserted at the plug (sealing lip attachment point) and the tip of the sealing lip. Relative to a triangle, we would speak of the bisector of an angle in this case. Here, the angle that lies at the tip of the sealing lip is bisected. If the above-described line has an acute angle to the axis of the syringe, the function of the sealing lip is ensured. Also, integral behavior of "the bisector of an angle" or "the bisector of the mass" is conceivable. The surfaces of the sealing lip can be arched or indented; they can have bulges or notches; they can be thickened at the tip like a hammer or an axe. It is essential to compare the resultant forces that arise when pressure is applied at the sealing lips in the distal direction. These resulting forces are easy to determine, and it does not matter what shape the sealing lip has. The distal direction is the preferred direction of the sealing lips, but the proximal orientation is also possible. Such a proximally oriented sealing lip definitely fulfills the sealing function to a certain extent.

Elasticity area:

It is important that the sealing lip press against the inside wall of the cylinder with a force that is perpendicular to this inside wall. Unlike in the case of the beads of the prior art, with the sealing lips this force is obtained from elastic forces that are caused by a deformable area, which does not lie on the perpendicular line to the inside wall of the cylinder and which lies through the contact area between the sealing lip and the inside wall of the cylinder.

Pulling zone and compressing zone:

The sealing lips are pressed under prestressing against the inside wall of the barrel. For this purpose, a force is necessary that is caused by an elasticity zone of the sealing lip. In this case, this elasticity zone receives both tensile forces and shearing forces. Relative to the length of the sealing lip, a force that has a lateral action relative to the inside wall of the cylinder is used. In this case, it is important that the plug behave in a static manner. In this case, only a pressing-together of beads or thickenings that press against the inside wall of the cylinder is known from the prior art. Only if the plug in the prior art moves is a shearing force also exerted on the bead, which can also produce a pulling zone at this plug. It thus is important that the tensile forces and shearing forces run approximately parallel to the axis of the syringe. When there is movement of the plug, regardless of whether the movement is new or old, tensile forces and shearing forces that run approximately perpendicular to the axis of the syringe are again exerted by the shearing force.

Materials of the plug:

The substance polytetrafluoroethylene is the substance that is known as TEFLON®. TEFLON® has remarkable properties, i.e., above 300° C., a minor weight loss occurs only gradually, and only above 400° C. is TEFLON® destroyed. TEFLON® has a low coefficient of friction of on the average 0.3; the coefficient of adhesive friction is 0.05 to 0.1 higher. In this case, pressure and sliding speed play no role. It is especially advantageous that even after prolonged storage, no high "tear-off and start-up moments" arise in comparison to other elastomers. Parts produced from teflon are physiologically harmless. During feed tests on animals, no harmful effects have been observed upon ingestion of TEFLON®. TEFLON® meets the FDA regulations concerning contact with food. TEFLON® is. The term syringe comprises the terms cartridge (large-volume syringe with at least 100 ml of volume), ampoule syringes, disposable syringes, disposable cartridge-needle units, one-time cartridge-needle units, one-time syringes, injection ampoules, disposable cartridge-needle units, ampoules that are ready for spraying, cylinder ampoules, double-chamber cartridge-needle units, two-chamber syringes, two-chamber cartridge-needle units, two-chamber syringes, and emergency syringes.

Lubricant:

Lubricants are intended to allow the plug to move inside the cylinder without significant expenditure of force. Preferred is silicone oil, which has the following properties: viscosity of at least 1000 cSt for plastic syringes and 300–400 cST in the case of glass (stoving siliconization); Grade: medical grade.

In industrial-property rights and technical and scientific publications, the step of siliconization is not mentioned in detail. It is wrong to conclude, however, that this step has been omitted. Rather, siliconization is a mandatory step, without which syringe use and therefore also syringe production cannot exist.

All publications are thus to be read from the standpoint of general technical knowledge. In this case, it is to be noted that the siliconization step is always included as a mandatory procedure. That this goes without saying is clear from DIN Standard 13 098, Part 1 under Item 4.4. Here, reference is made to the mandatory siliconization of disposable syringes. For prefilled disposable syringes, the standard is not mandatory, but it can also be used since no different standard opposes this DIN Standard 13 098.

Material of the plug and the syringe:

Plastics are presented in detail in Römpps—Chemie—Lexikon, publishers Jürgen FALBE and Manfred REGITZ, 9th Edition, Stuttgart, 1990 on pages 2398 ff. COC, PP, and polymethylpentene are preferred. [COC=cycloolefin copolymer with the trademark name CZ (manufacturer: Nihon Zeon) and TOPAS (manufacturer: Mitsui Chemicals and Hoechst)]. These plastics are especially suitable for use in prefilled, terminally sterilized syringes since their high melting points (at least 130° C.) allow steam sterilization (standard process 121° C.). Moreover, the optical properties for a one-hundred-percent visual inspection according to the pharmacopeia are adequate.

Shape of the plug:

Advantageous is a syringe in which the plug is guided in such a way that the axis of the plug basically coincides with the axis of the syringe. Guiding can be ensured by guide fins or guide sliding surfaces at the plug. These parts have the purpose of preventing the plug from tilting and orienting the plug in such a way that the axis of the plug and the axis of the syringe can deviate from one another only insignificantly. It is also possible for the plug to be attached with a plunger, which itself is guided or which has a guideway in which the plunger can move. Deviations of the axes (plunger and barrel) of up to 10°, preferably 5°, more preferably 3°, are, however, easily managed.

Syringes:

Glass syringes and plastic syringes are described in detail in the publication by Junga (M. JUNGA (1973) Pharm. Ind. Vol. 35, No. 11a, pages 824 to 829). A mixture of glass and plastic is presented in WO 96/00098 (date of application Jun. 23, 1995). extremely hydrophobic and repels water almost completely. For this purpose, it is ensured that interaction between the medium and the plug is impossible. Owing to the thickness of the plug, the diffusion of gases from the outside toward the inside and from the medium from inside toward the outside is negligible.

As a variant, polyethylene is at least partially substituted. In this case, the hydrogen atoms are at least partially replaced by fluorine atoms. This can be a polytetrafluoroethylene or a derivative thereof in which not all hydrogen atoms are substituted.

Shape of the syringes:

The syringes are usually rotationally symmetrical; only the finger holders and device holders and occasionally also the syringe outlet piece deviate from symmetry. Thus, the syringe outlet piece can be arranged eccentrically. Especially preferred is the Luer lock since it is used exclusively in the administration of contrast media if mechanical pumping devices are used. Also, in the case of manual administration, the Luer lock and the associated tube prevent unintended movements by the physician from being directly transferred to the cannula. In addition, the simple Luer nozzle and also the record nozzle are known.

It is also possible to bond the syringe outlet piece and thus to seal it. It is then advantageous for a syringe outlet piece to have a predetermined point of break, which makes it easy to open the syringe outlet piece before use.

Syringe outlet piece:

The proximal and distal ends of the syringe must be sealable. The distal end is sealed by a closure that can be attached to the syringe outlet piece. The syringe outlet piece comprises the cover of the barrel in this industrial-property right. In addition, the syringe outlet piece comprises a pipe that leads to the needle or the hose and an end piece that comes into contact with the needle or the hose and surrounds a cylinder with screw thread on the inside, whereby the cylinder surrounds the end piece and has a screw thread for, e.g., a Luer lock. In this case, the syringe outlet piece can be one-piece or multi-piece. The cover can be arched, flat, or pyramid-shaped. Mixed forms are also conceivable. The plug seals the proximal end of the syringe. It must be able to slide in the cylinder, and the medium must be reliably protected from the environment. It is to be as impermeable as possible to gases and liquids.

Temperature fluctuations must be dampened without disruption of function. Usually, when the syringe is mechanically emptied, the plug is not provided with a separate plunger. Rather a plunger that is part of the pumping device engages in a closure inside the plug, so that the plug can move easily. (Cf. EP 0 584 531)

Proximal and distal:

The terms proximal and distal are defined from the standpoint of the attending physician. At the distal end is the syringe outlet piece to which is connected, for example, the cannula or a hose, which leads to a cannula. At the proximal end is the plug which presses the medium through the distal end during administration. The plug can be moved manually or else mechanically. The term plug also comprises the plunger. For manual evacuation of the syringe, it is helpful to the operator if the syringe has finger holders at the proximal end. In this case, the finger holders usually have at least one surface as a support for the index finger and the middle finger, whereby the surface of the finger holder is basically perpendicular to the axis of the barrel. In the case of mechanical pumping devices, various models are known. A syringe then has preferably one or more device holders preferably at the proximal end. Such a mechanical pump is especially well described in EP 0 584 531 (Reilly et al., date of application Jul. 21, 1993). Mixed forms of finger holders and device holders are also possible.

Medium:

The medium in the filled syringe is a mixture of a fluid medium and at least one gas. In this case, the gas volume is to be as small as possible; desirably, it is a gas volume that has a value of zero. The medium can be a liquid, a solution, a suspension, or an emulsion. These forms of phenomena are described in W. SCHROTER et al., (1987) Chemie; Fakten und Gesetze [Chemistry; Facts and Laws], 14th Edition, Leipzig on pages 23 ff.

Preferred is a fluid medium that is a contrast medium. These are the following contrast media with the generic names: amidotrizoic acid, gadopentetic acid, gadobutrol, gadolinium EOB-DTPA, iopamidol, iopromide, iotrolan, and iotroxic acid.

Dynamic Pressure Gain

Very preferred is the syringe according to the invention in which at least one surface or the mass-resultant of the sealing lip faces distally. For this purpose, corresponding pressures are built up since with the dynamic behavior of the sealing lips, the application pressure is increased by the pressure increase in the lumen of the syringe.

The sealing lip is preferably annular.

Preferred is a medical syringe according to the invention in which the sealing lip is sealed tightly against the inside wall of the syringe when there is pressure in the distal direction.

More preferred is a medical syringe in which the sealing lip is sealed tightly against the inside wall of the syringe when there are movement and pressure in the distal direction, whereby the pressure inside the syringe in the volume that is prepared for receiving free-flowing medium is greater than in the compartment,
which
α) is formed either by the inside wall of the cylinder and plug wall, or
β) by the inside wall of the cylinder and the open proximal end.

The pressure with which the sealing lips are forced against the inside wall of the syringe increases when there is pressure on the plug in the distal direction. Preferably, this increase in the application pressure is linear, optionally at low pressures large and later dropping off. In this case, the sealing lip acts like a lip valve or gliding valve.

Preferred is a syringe according to the invention in which the sealing lip faces in the direction toward the distal end and has a surface which faces toward the axis of the syringe and which passes on the force that is produced by the internal pressure of the syringe (during use or during autoclaving) toward the inside wall.

Minimization of Residual Volume

Medical syringes according to the invention, whereby the plug is configured complementarily to the shape of the distal end of the syringe, are advantageous for reducing a residual volume that cannot be removed from the syringe despite complete pressing-in of the plug.

Preferred is a medical syringe according to the invention, whereby the plug has a convex, planar, or concave design, or else has pyramid-shaped, cone-shaped, truncated-pyramid-shaped, truncated-cone-shaped, or hemispherical configurations, whereby the bulge faces distally or proximally, depending on the design of the end of the syringe.

Disposable syringes are preferred.

Contact Pressure Gain

Preferred is a syringe according to the invention in which the sealing lip, which runs at least partially axially parallel to the inside wall of the cylinder, has a reinforcement piece or material thickening,
which is connected to the sealing lip attachment point at the plug via a plasticity area and/or elasticity area.

Preferred Material

Preferred are syringes according to the invention in which the polytetrafluoroethylene is a TFM, which has the following properties:

Elongation at tear of greater than 500%, deformation under load of less than 10%, SVI value of less than 250, permeability of sulfur dioxide of less than 310 at a film thickness of 1 mm, permeability of hydrochloric acid of less than 600 at a film thickness of 1 mm, and permeability of chlorine of less than 300 at a film thickness of 1 mm.

The values are measured according to the following standards:

Elongation at tear according to ISO 12086, deformation bacg ASTM D 621,

SVI value ISO 12086, permeability according to DIN 53380 at a film thickness of 1 mm.

More preferred is a syringe according to the invention in which the plug is made of one substance.

Still more preferred is a syringe according to the invention in which the plug has a modulus of elasticity of 550±100 N/mm$^2$ at 25° C.

Most preferred is a syringe according to the invention in which the plug has an adhesive friction value of $\mu_r$=0.35±0.05 and a sliding friction value of $\mu$ 0.3±0.05.

Filled, Sterilized syringes

Preferred is a syringe according to the invention in which the syringe is filled with a medium and can be autoclaved.

More preferred is a syringe according to the invention in which the syringe can be autoclaved in the presence of a supporting pressure.

It is useful for at least the syringe body to be cast or sprayed in a sterile room at at least 250° C.

A syringe according to the invention in which the sterile syringe can be packed into a sterile container that has at least one gas-permeable, but not germ-permeable, wall is advantageous.

Explanation Regarding Sterilization

A syringe must be cleaned of impurities. All particles that are not made of the material of the syringe and the medium and that are the detached fragments of the syringe are impurities.

Pyrogens are substances that as fragments of bacteria trigger an immunologic response in humans. In particular, these are lipopolysaccharides, i.e., cell-wall components of gram-negative bacteria.

As chemical sterilization processes, treatment with ethylene oxide, propan-3-olide, and diethyl dicarbonate, in addition to hydrogen peroxide and an ozone/steam mixture, are known.

Also, sterilization with high-energy radiation is possible. Here, gamma rays and x-rays are known.

The syringe or cartridge is heat-sterilized in an autoclave or sterilizer with hot air or with microwaves.

To keep the plug from moving inside the cylinder, it is advantageous if the plug is attached during sterilization.

It is optionally possible to build up supporting pressure in the sterile room of the autoclave or the sterilization chamber by a gas in the sterile room, whereby the pressure on the outside surface of the syringe is greater than, equal to, or less than the pressure on the inside surface of the syringe. The supporting pressure can be defined as the pressure that corresponds to the sum of the partial pressures in the sterile room minus the partial pressure of the steam.

In addition, it is advantageous that the filled and terminally filled syringe is packaged in sterile plastic film and/or aluminum foil under optionally aseptic conditions. In this case, it is advantageous that the syringe may be packaged in sterile blisters, whereby optionally aseptic conditions are present.

Process for the Production of a Prefilled Sterile Syringe

The invention also comprises a process for the production of a prefilled sterile syringe, which comprises the following features.

a) sterile production of the syringe parts or cleaning and sterilization of the syringe parts that are produced, b) assembly of the parts,
  (i) in this case, the distal end is closed when the syringe is filled from the proximal end, or
  (ii) the proximal end is closed by the plug when the syringe is filled from the distal end, c) optionally sterilization of the assembled syringe, d) proximal or distal filling, dep ending on the opening that remains, e) proximal closing by the plug or distal closing by an outlet closure or bonding of the outlet, f) sterilization of the filled and closed syringe, g) optionally sterile packaging of the syringe in a container with at least one surface that is gas-permeable but not germ-permeable.

Such processes are described in detail in EP 0 227 401, EP 0 553 926 and U.S. Pat. No. 5,207,983. Reference is also made to the bibliographic reference of E. Venten and J. Hoppert, Pharm. Ind. Vol. 40, No. 6 (1978). In this publication, including the literature cited therein, sterilization methods are considered in detail. The publication by Venten and Hoppert is part of the application by citation. It is especially advantageous if a combination of the syringes according to the invention and an administration device consists of an injectomat and connections, whereby the injectomat is a pumping system, and the connections connect the outlet of the syringe to the patient. Such an injectomat is described in, e.g., EP 0 192 786.

Combination of Syringe and Injectomat

In addition, the invention comprises a combination of a prefilled, terminally sterilized syringe according to the invention and an administration device made of injectomats and connections, whereby the injectomat is a pumping system and the connection connects the outlet of the syringe to the patient. Such a pumping system is described in publication EP 0 584 531.

BRIEF DESCRIPTION OF THE DRAWINGS

The preferred embodiments of a syringe according to the invention can be seen in the figures. The invention is not limited to these embodiments.

DETAILED DESCRIPTION

Figure 1A:
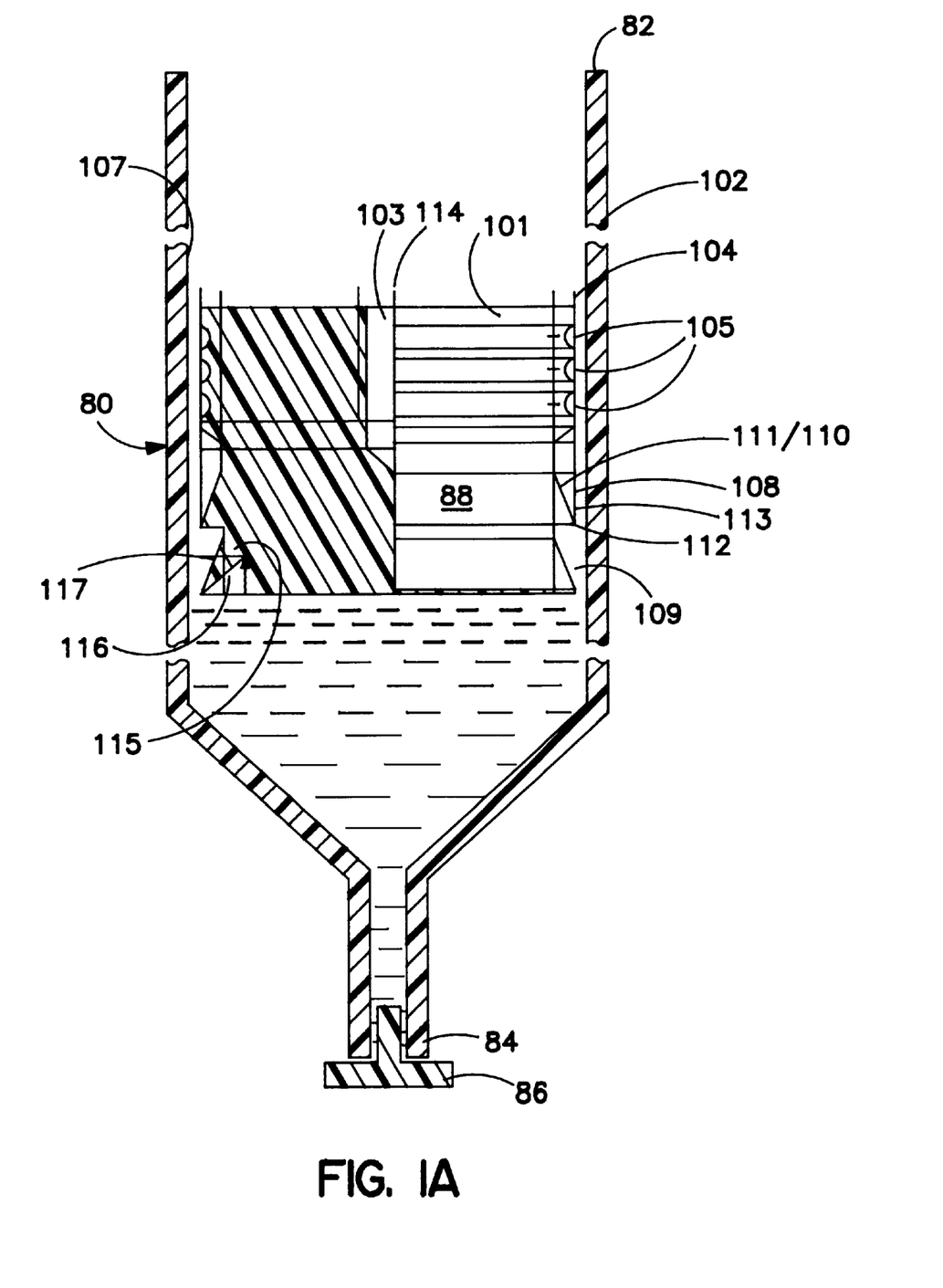
FIG. 1A is a side elevation of the plug of FIG. 1B in a syringe which includes a distal end sealed by a cover.
Figure 1B:
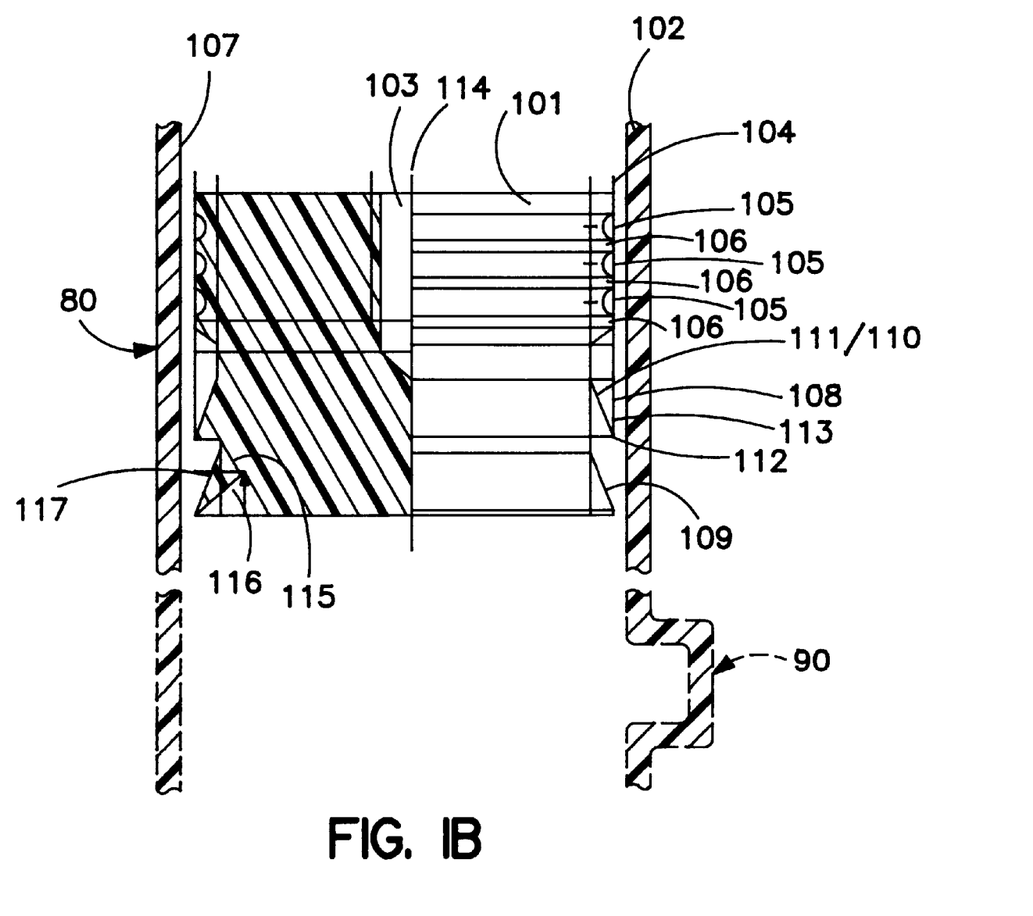
FIG. 1B shows a cross-section through a TEFLON® plug in a barrel having in dotted lines an optional outward bulge.

FIG. 1A discloses a syringe 80 having a proximal end 82 and a distal end 84. The syringe has a cylinder cover 86 over the distal end 84. The proximal end 82 is open and is sealed by a plug 101 which had a body portion 88 formed about an axis 114. In FIG. 1B, an optional bulge 90 is shown.

FIGS. 1A and 1B, which is the preferred embodiment, shows a cross-section through a plug 101, which is arranged in a barrel 102. Plug 101 consists of a core 103, which has three notches 105 on plug cylinder edge 104, which have the shape of a partial circle. Notches 105 do not directly abut one another, but are connected by webs 106, which directly adjoin inside wall 107 of the cylinder.

Then below, i.e., facing toward the medium and away from the plunger, there are two sealing lips 108 and 109, which are arranged behind one another. Proximal sealing lip 108 forms an orthogonal triangle, whereby side 111 that is adjacent to the acute angle, which is proximal, is formed by cylinder wall 110 of plug 101, opposite side 112 is formed by a radially projecting side, and hypotenuse 113 is formed by a side that faces plug axis 114 obliquely. Hypotenuse 113 adjoins cylinder inside wall 107 only in a small area, which adjoins opposite side 112.

Distal sealing lip 109 has a triangular shape, whereby base 115 provides a root of the sealing lip which is arranged obliquely to plug axis 114 and extends at an obtuse angle with respect to the axis. Two almost identical legs 116 and 117 emerge from base 115 and extend at acute angles with respect to the axis 114 so that the sealing lip 109 extends obliquely with respect to the axis 114. Only the leg 117 that has a surface 117a which faces away from plug axis 114 touches cylinder inside wall 107. Because of the material, two sealing lips 108 and 109 are elastic; they also press lightly on cylinder inside wall 107 in the at-rest position.

Figure 2:
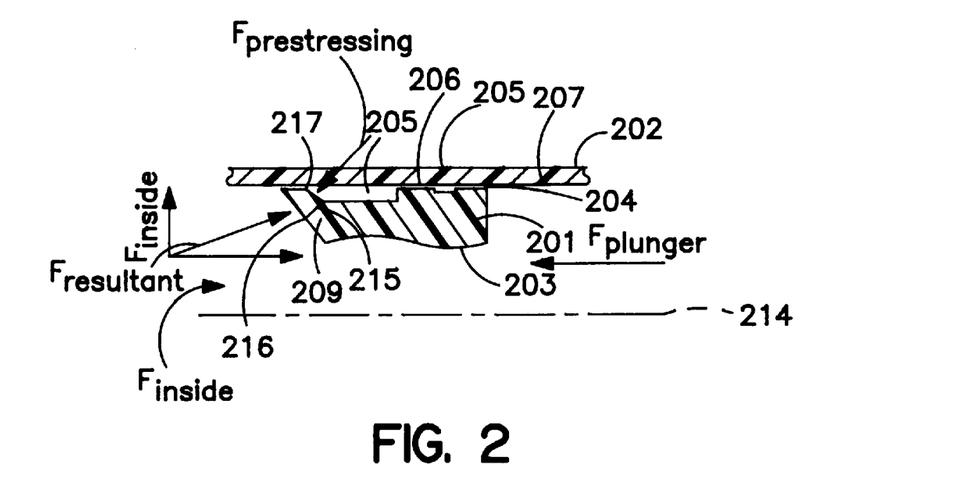
FIG. 2 shows, in cross-section, the force ratios at the sealing lip.

FIG. 2 shows the main force ratio in a plug 201 according to the invention. It is a cross-section through plug 201, which is arranged in a barrel 202. Plug 201 consists of a core 203, which has two notches 205, which are rectangular, at plug cylinder edge 204. Notches 205 do not directly adjoin one another, but are connected by a web 206, which directly adjoins cylinder inside wall 207.

Sealing lip 209 has an almost triangular shape, whereby base 215 is arranged obliquely to plug axis 214. Two almost identical legs 216 and 217 emerge from base 215, whereby only the leg that faces away from plug axis 214 touches cylinder inside wall 207. Because of the material, sealing lip 209 is elastic; it also presses lightly on cylinder inside wall 207 in the at-rest position.

The forces on sealing lip 209 are designed differently in the dynamic and static states. The dynamic state exists if pressure is exerted on the plunger, so that plug 201 is pressed in the distal direction. In this case, the syringe internal pressure of the medium is increased. In a static state, neither the medium nor the plunger exerts pressure on the plug, which is in equilibrium. If the coefficient of friction were infinitely small, the plunger, if no forces acted on it, would be free in this position.

Sealing lip 209 has a light prestressing; it thus easily adjoins cylinder inside wall 207. Since the contact pressure surface is very small, the surface pressing power is still relatively high. In the static state, plug 201 thus adequately seals the interior space of barrel 202. In this case, small forces are used. Small forces also mean, however, that the cold-flow behavior of the polytetrafluoroethylene is not stressed. Such a syringe can be stored for a long time without the material of plug 201 being noticeably deformed by cold flow.

In the dynamic state, plug 201 is pressed in the distal direction, and pressure builds up in the medium. The latter presses on leg 216 that faces inward, thereby forcing the mass of sealing lip 209 outward. On the one hand, the force is caught by base 215, and, on the other hand, by the front part of outside leg 217. Especially the last-mentioned part has the effect that the pressure of lip 209 on cylinder inside wall 207 is very high per unit of surface area. In this case, the surface area is large enough to successfully prevent the medium from overflowing from the lumen of the syringe into the ambient space. Since webs 206 are not basically sealing, atmospheric pressure, which differs from the internal pressure of the syringe, is exerted on leg 217 that faces outward.

Figure 3:
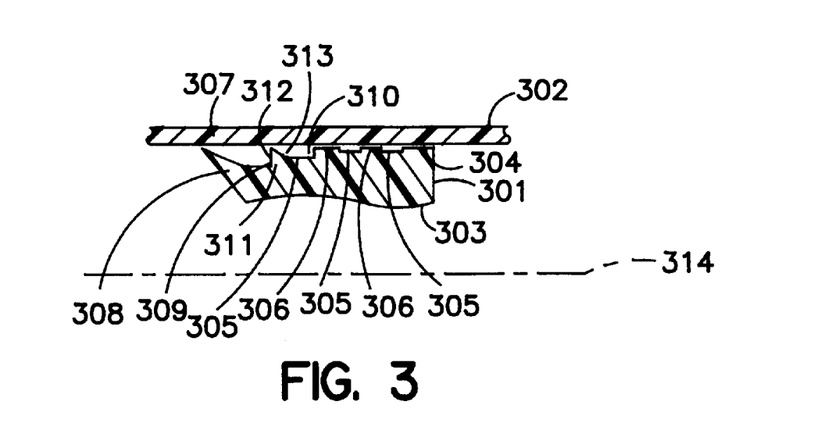
FIG. 3 shows a cross-section through a plug part with two sealing lips.

FIG. 3 shows a cross-section through a plug 301, which is arranged in a barrel 302. Plug 301 consists of a core 303, which has three notches 305, which are rectangular, on syringe cylinder edge 304. Notches 305 do not directly adjoin one another, but are connected by webs 306, which directly adjoin cylinder inside wall 307.

Then there are two sealing lips 308 and 309 that are distal, i.e., facing toward the medium and away from the plunger and which are arranged behind one another. These two sealing lips 308 and 309 form an orthogonal triangle, whereby sides 311 that are adjacent to the acute angle, which faces proximally, are formed by cylinder wall 310 of plug 301, opposite sides 312 are formed by a radially projecting side, and hypotenuses 313 are formed by a side that faces obliquely toward plug axis 314. Hypotenuses 313 adjoin cylinder inside wall 307 only in a small area, which adjoins opposite side 312.

Figure 4:
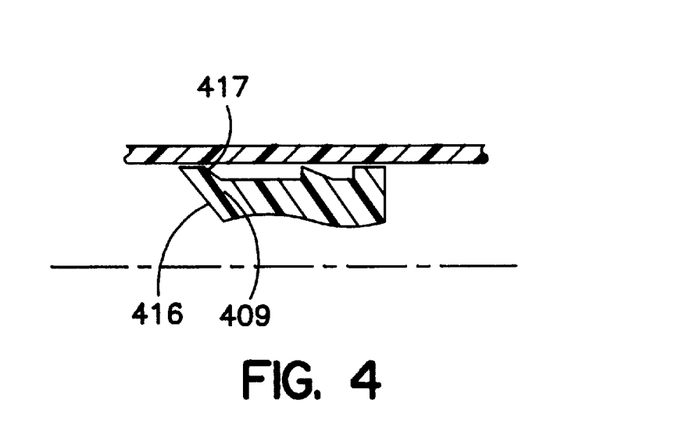
FIG. 4 shows a cross-section through a biconcave sealing lip.

FIG. 4 shows, in a different way, a sealing lip 409, which has a convex shape both in outside leg 417 and in inside leg 416.

Figure 5:
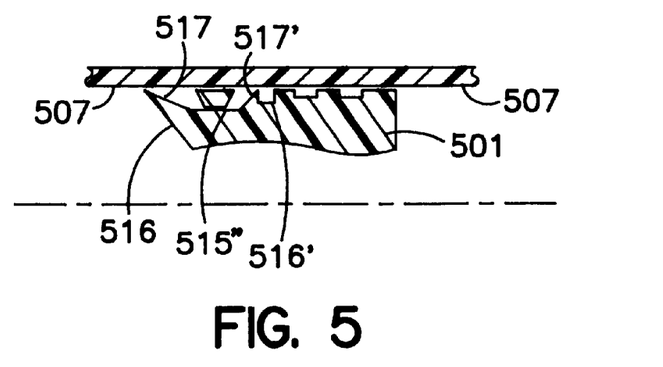
FIG. 5 shows a cross-section through two sealing lips that face in different directions.

FIG. 5 shows three sealing lips, one which with two legs 516 and 517 faces distally, and one which with two legs 516′ and 517′ faces proximally. In between the two there is a dovetail-shaped web, which also exerts a sealing action when there is dynamic movement of plug 501 since, owing to elastic base 515″, it buckles lightly against the direction of movement and is pressed by its contact area, facing in the direction of movement, against cylinder inside wall 507.

Figure 6A:
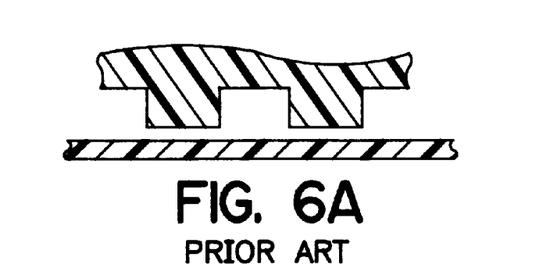
FIG. 6A shows a cross-section through two sealing thickenings.

FIG. 6A shows a seal according to the prior art. In this connection, the spatial distribution of the webs relative to the surface pressure at certain points of the web at the cylinder inside wall is represented. As is seen in FIG. 6B, the surface pressure is distributed over a sizeable area, and in this case has a point pressure that is relatively low.

Figure 7A:
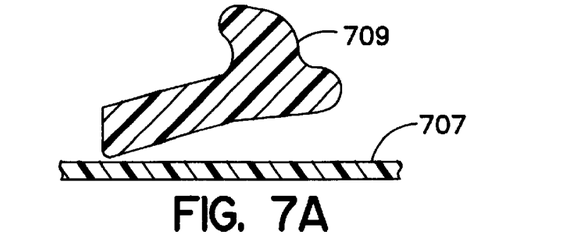
FIG. 7A shows a cross-section through a sealing lip.

FIG. 7A shows a sealing lip 709 according to the invention, which owing to its shape has only a small contact surface with cylinder inside wall 707. As is seen in FIG. 7B, relatively great pressure is exerted at certain points, but in this case the entire surface that adjoins cylinder inside wall 707 is smaller.

Figure 6B:
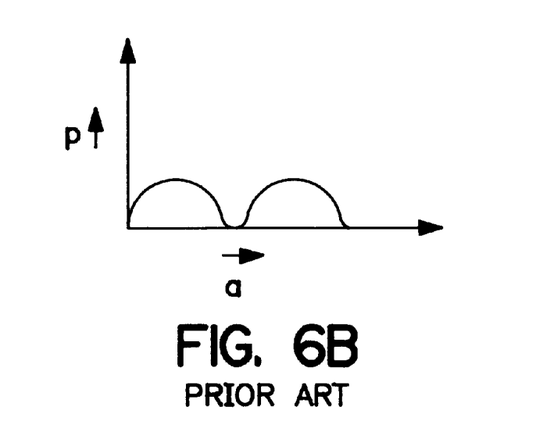
FIG. 6B shows the related pressure/surface area diagram.
Figure 7B:
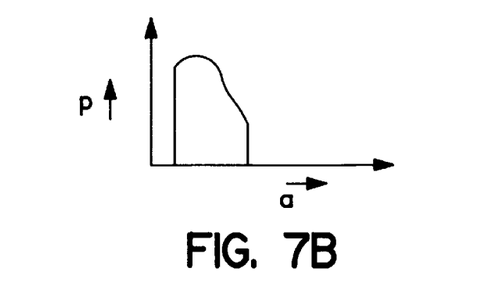
FIG. 7B shows the related pressure/surface area diagram.

The dotted surfaces in FIGS. 6 and 7 should be equally large relative to the integral. The basic difference is that in FIG. 7, the surface application force is greater than in FIG. 6. In addition, and this is the most important point, this pressure-surface area diagram shows only the static state.

In the dynamic state, whereby the medium is compressed in the syringe, considerably higher values occur in FIG. 7; conversely the values in FIG. 6 remain the same quantitatively, and at most move proximally in their position.

Figure 8:
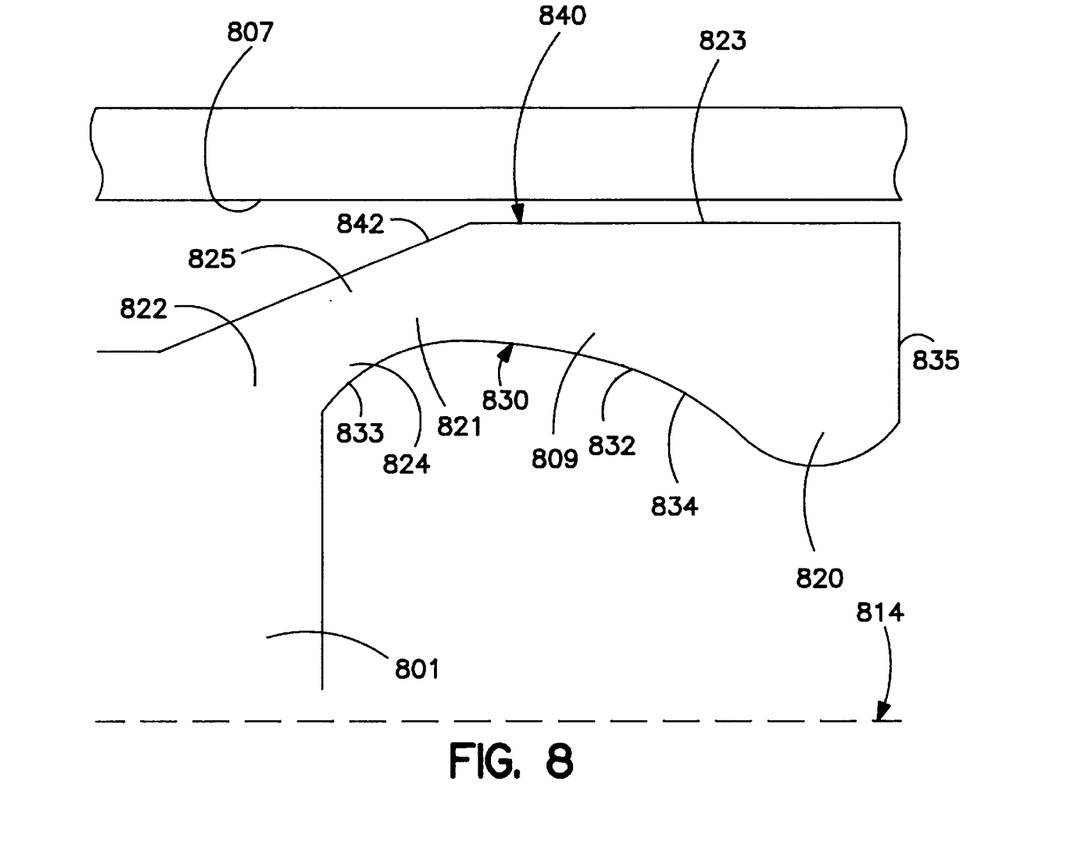
FIG. 8 shows a cross-section through a sealing lip with a reinforcement piece.

FIG. 8 shows a cross-section through a plug 801 with a sealing lip 809, which adjoins cylinder inside wall 807. Sealing lip 809 does not end with an acute taper, but has a thickening 820. In addition, the elasticity zone and plasticity zone 821, which is between sealing lip projection point or base 822 and contact surface 823 between sealing lip 809 and cylinder inside wall 807, can be clearly seen from FIG. 8. In addition, the elasticity zone and plasticity zone 821 are arranged between sealing lip projection point or base 822 and thickening 820. In the area of the elasticity zone, there are a compressing zone 824 and a pulling zone 825, which both run approximately parallel to plug axis 814. In addition, it can be seen that elasticity zone 821 is not on the perpendicular lines to cylinder inside wall 807; said perpendicular lines pass through contact surface 823 simultaneously. Plasticity zone 821 plays a role when a constant pressure or thermal stress acts on sealing lip 809, as occurs especially in autoclaving. This area exhibits flow behavior, without sacrificing the entire elasticity of the sealing lip at the same time. The balanced relationship between plasticity and elasticity in this area 821 is essential to successfully seal the plug. The forces and changes that arise in this case can be easily checked by one skilled in the art by tests.

The sealing lip 809 has a first surface 830 which includes an arcuate surface 832 which curves outwardly at 833, inwardly at 834 and outwardly again at 835 as it progresses from the base 822 to the contact surface 823. The contact surface 823 forms an axially extending portion of a second surface 840 which is joined to the base 822 by a connecting surface 842.

We claim:

1. A syringe for injecting a fluid medium wherein the syringe has a selected shelf life, comprising:

a hollow cylinder of plastic or glass adapted to contain the fluid medium, the cylinder having a smooth cylindrical inner wall surface, a distal end with an outlet and a proximal end for receiving a plunger shaft therethrough;

a cylindrical plug having a body portion with an axis, the plug being disposed for sliding movement in an axial direction within the hollow cylinder toward the distal end, the plug being adapted to eject the fluid medium from the hollow cylinder by pushing the medium with a distal face of the plug which is adapted to engage the medium;

the plug having a non-sealing substantially cylindrical portion disposed adjacent to the smooth cylindrical inner wall or surface;

an annular lip obliquely ex ending in a radial and axial direction from the body portion of the plug, the obliquely extending annular lip having a first surface forming part of the distal face of the plug which is adapted to engage the fluid medium; a second surface which directly touches the smooth cylindrical inner wall surface of the hollow cylinder, and a third surface joining the plug body at a location axially spaced from the first surface to define a root of the lip where the first and third surfaces join the body of the plug; elastic forces in the lip when the plug is at rest with the cylinder having a tension zone in one surface and a compression zone in another surface;

at least the annular lip being made of a material selected from the group consisting of polypropylene and polyethylene, wherein the hydrogen atoms of the polypropylene and polyethylene are at least partially replaced by fluorine atoms resulting in polyfluoropropylene and polyfluoroethylene;

whereby the lip experiences insignificant cold flow during storage so that a selected plug remains sealed during the shelf life of the syringe and the plug does not have excessive frictional drag when used after storage during the shelf life.

2. The syringe of claim 1, wherein the plug further includes a rigid rib disposed on the plug in axial spaced relation with the lip between the lip and cylindrical portion.

3. The syringe of claim 2, wherein the plug further includes a plurality of axially spaced circumferential grooves in the substantially cylindrical portion.

4. The syringe of claim 1, wherein the plug further includes a plurality of axially spaced circumferential grooves in the substantially cylindrical portion.

5. The syringe of claim 4, wherein the first surface of the lip extends at a first acute angle with respect to the axis of the plug and the send surface of the lip extends at a second acute angle with respect to the axis of the plug, which second acute angle is less than the first acute angle with the base of the lip extending at an obtuse angle with respect to the axis of the plug.

6. The syringe of claim 1, wherein the first surface of the lip extends at a first acute angle with respect to the axis of the plug and the second surface of the lip extends at a second acute angle with respect to the axis of the plug, which second acute angle is less than the first acute angle with the base of the lip extending at an obtuse angle with respect to the axis of the plug.

7. The syringe of claim 4, wherein the first surface includes an arcuate portion which curves outwardly, then inwardly and outwardly again as it progresses from the base of the lip to the second surface; wherein the second surface has a substantial axial length extending parallel to the inner wall for sealing engagement therewith and a connecting surface which extends at an acute angle back toward the root of the lip, with the base defining an obtuse angle with the axis of the plug.

8. The syringe of claim 1, wherein the first surface includes an arcuale portion which curves outwardly, then inwardly and outwardly again as it progresses from the root of the lip to a second surface; wherein the second surface has a substantial axial length extending parallel to the inner wall for sealing engagement therewith and wherein the third surface extends at an acute angle back toward the root of the lip, with the root defining an obtuse angle with the axis of the plug.

9. The medical syringe according to claim 1, wherein the sealing lip runs at least partially in an axial direction parallel to the axial direction of the cylindrical inside wall, and wherein the sealing lip has a reinforcement defined by the thickener material that is connected to the sealing lip via a plasticity area or elasticity area.

10. The medical syringe according to claim 1, wherein the material of the plug has the following properties:

elongation at tear of greater than about 500%, deformation under load of less than about 10%, SVI value of less than about 250, permeability of sulfur dioxide of less than about 310 at a film thickness of 1 mm, and permeability of hydrochloric acid of less than about 600 in the case of a film thickness of 1 mm and permeability of chlorine of less than about 300 at a film thickness of 1 mm.

11. The medical syringe according to claim 1, wherein the plug is made of a single substance and is unitary.

12. The medical syringe according to claim 1, wherein the material of the plug has a modulus of elasticity of about 550±100 N/mm$^2$ at 250° C.

13. The medical syringe according to claim 1, wherein the plug has an adhesive friction value $\mu_t$ of about 0.35±0.05 and a sliding friction value $\mu$ of about 0.30±0.05 with respect to the cylindrical inner wall surface.

14. A medical syringe comprising:

a hollow cylinder of glass or plastic with an inner wall surface, a proximal end and a distal end, the cylinder being adapted to contain an injectable material;

a plug within the hollow cylinder adapted to push the injectable material from the cylinder through the distal end and for sealing the proximal end, the plug being unitary and made of polypropylene or polyethylene wherein the hydrogen of the polypropylene and polyethylene are at least partially replaced by fluorine atoms resulting in polyfluoropropylene and polyfluoroethylene;

the plug having a cylindrical portion not in sealing relation with the inside cylindrical wall and an annular lip in sealing engagement with the wall, the plug material having a modulus of elasticity of about 550±100N/mm$^2$ at 25°, an adhesive friction value $\mu_t$ of about 0.35±0.05 and a sliding friction value $\mu$ of about 0.30±0.05 with respect to the cylindrical inner wall surface.

15. The medical syringe according to claim 14, wherein the material of the plug has the following properties:

elongation at tear of greater than about 500%, deformation under load of less than about 10%, SVI value of less than about 250, permeability of sulfur dioxide of less than about 310 at a film thickness of 1 mm, and permeability of hydrochloric acid of less than about 600 in the case of a film thickness of 1 mm and permeability of chlorine of less than about 300 at a film thickness of 1 mm.

* * * * *